United States Patent [19]

Herstein

[11] Patent Number: 5,118,496
[45] Date of Patent: Jun. 2, 1992

[54] COATED COSMETIC MATERIALS AND METHOD OF COATING COSMETIC MATERIALS

[76] Inventor: Morris Herstein, P.O. Box 209, Scarsdale, N.Y. 10583

[21] Appl. No.: 591,815

[22] Filed: Oct. 2, 1990

[51] Int. Cl.⁵ .................. A61K 7/04; A61K 7/13; A61K 9/14; A61K 9/50
[52] U.S. Cl. ........................... 424/63; 424/61; 424/401; 424/489; 424/490; 424/497; 514/844
[58] Field of Search .................. 424/401, 61, 63, 489, 424/490, 497; 428/900; 514/844

[56] References Cited

U.S. PATENT DOCUMENTS

| | | | |
|---|---|---|---|
| 3,697,653 | 10/1972 | Ongley | 514/63 |
| 4,197,347 | 4/1980 | Ogawa | 428/900 |
| 4,455,691 | 6/1984 | Van Aken Redinger | 528/42 |
| 4,832,944 | 5/1989 | Socci | 424/61 |

*Primary Examiner*—Thurman K. Page
*Assistant Examiner*—Carlos Azpuru
*Attorney, Agent, or Firm*—Handal & Morofsky

[57] ABSTRACT

An improved coating for cosmetic materials is disclosed. Flouroalkylpolysiloxanes used as coatings for cosmetic powders and microparticulate materials provides the advantages of existing polysiloxane coatings plus provides advantages making the coated materials useful in emulsion systems and alkaline systems even when aged at high temperatures.

9 Claims, No Drawings

COATED COSMETIC MATERIALS AND METHOD OF COATING COSMETIC MATERIALS

TECHNICAL FIELD

The present invention relates to cosmetic materials and improved cosmetic formulations resulting from coatings applied to powders and particulates used in cosmetic formulations.

BACKGROUND

The increasing importance of personal appearance, whether in projecting a healthy, youthful or stylish image, has led to an increasing demand for cosmetics. The demand is being met by a growing number of products and suppliers with an attendant expansion in competition.

Product quality is important and is reflected by many qualities and characteristics of each product. Physical appearance of the product should be homogeneous. Any streaking, settling or separation has an adverse impact on the consumer.

A cosmetic should apply smoothly, have a good skin adhesion and a good feel. A makeup that applies unevenly, flakes, smears or feels overly dry or oily is not likely to be favorably received.

Color consistency from batch to batch is also of importance. Small variances in shade are noticeable in cosmetics and accordingly a consumer's expectation in receiving the same shade as previously obtained should be fulfilled.

Cosmetics use varying amounts of particulates including pigments, pearlescent materials, extenders, etc., dispersed in oils, waxes and emulsions. Uniform dispersion, suspension stability and particulate loading in a suspension are all factors affecting the product quality. Obviously, optimization of all is desirable.

Problems are encountered in trying to improve one or two factors without adversely affecting another or improving desired characteristics without introducing other detrimental effects.

Coating of pigments, extenders and fillers has been used to enhance dispersion of particulates by increasing hydrophobicity. Increased hydrophobicity also aids in the suspension of particulates in cosmetic preparations.

Pigments have been treated with lecithin along with lecithin component fatty acids and related fatty acids. Metal alkoxides, metal soaps and metal salts of fatty acids have been used with success.

Silicone treatment of pigments is another method of treatment and results in improved hydrophobicity. Dispersion, suspension and loading characteristics are all improved as are the water repellence and spreadability of a product incorporating the treated pigment. Enhanced skin adhesion and reduced color change on skin are also benefits of silicone treatment.

Simethicone (dimethyl polysiloxane) has been widely used as a coating and is one of the simplest, structurally, of the silicones used. However, with all the advantages associated with silicone treatment, a problem common to all the silicones results in adverse characteristics in the final product, including the failure to have extended shelf life.

SUMMARY OF THE INVENTION

Hydrogen generation has been observed from the silicone treated pigments and the hydrogen generation may be pronounced in emulsion systems and alkaline systems. The hydrogen generation is severe enough to raise questions about whether the silicone treatment is desirable in such systems or where a long shelf life is required.

The invention is intended to provide a remedy to this problem. It solves the problem of how to achieve desired results in optimizing cosmetic characteristics without introducing some of the known drawbacks of existing formulations.

Silicone treatment achieves many desired advantages for incorporating pigments and other cosmetic materials in cosmetic products. Certain silicone structures have been modified and result in coatings that are useful without the drawback of hydrogen production.

BEST MODE FOR CARRYING OUT THE INVENTION

In principle, substitution for the methyl units in simethicone will retain the silicone-oxygen backbone of the silicone structure. The beneficial effects as a coating can also be retained. However, the substitution of hydrogen or an alkyl group for the methyl group does not improve the hydrogen generation problem.

Moreover, substitution of a non-halogen, other than hydrogen or an alkyl group, for the methyl group can adversely affect the hydrophobicity of the compound.

Substitution with halogens can preserve the hydrophobicity but may also produce diatomic halogen gas or a gaseous hydrogen halide acid in addition to the hydrogen gas. Flourine has, however, in some instances been found to behave differently in this respect from the other halogens.

In accordance with the present invention, it has been found that flourine combined with carbon in a terminal methyl group extending from, but not directly bonded to, a silicone atom has been found to produce an extremely stable compound. More particularly, flouroalkyl-, diflouroalkyl- and triflouroalkylpolysiloxanes, in accordance with the invention, all show great stability and avoid the problem of hydrogen generation. Flouroaklyl- polysiloxanes where the flourine is on a terminal methyl group of up to a 10 carbon alkyl group bonded to a silicone atom are also effective. Flourine may be present on more than one methyl group as long as the methyl group bonded to the silicone backbone is not flourine bearing.

Triflouroalkylpolysiloxanes are commercially available from Grant Industries, Inc. under the name Gransil and have proved most satisfactory in coating pigments, extenders, pearlescents and filler material for cosmetics.

It is also been discovered by experimentation that the flouroalkyl groups can be uniformly or randomly spread about the silicone-oxygen backbone. The flouroalkyl groups discourage hydrogen generation when as few as approximately one flouroalkyl group per ten silicone-oxygen units is present.

Dimethicone is represented by the formula:

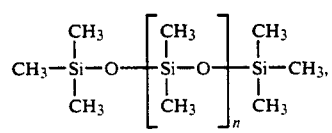

or even more basically as:

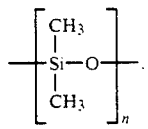

Substitution of a flourinated alkyl group of 2 to 10 carbons (—R—CF₃) for some methyl (—CH₃) groups in dimethicone to yield units of

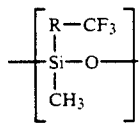

achieve the desired result. The terminal flourinated methyl group may be —CH$_2$F, —CHF$_2$ or —CF$_3$. Methyl (—CH$_2$—) units in the alkyl group R may also be flourinated as long as the initial methyl unit, that unit bonded to the silicone, is not flourinated. For example, polysiloxanes having units of

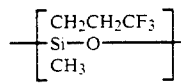

and others having

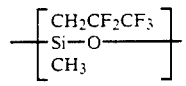

interspersed along the basic dimethicone structure have both proved very suitable The flouroalkyl-polysiloxane may average up to 500 or 1000 monomer units in length although units in the 1 to 500 range are preferred. Sub ranges of 1 to 100 and 100 to 500 are both very effective.

Alkyl units up to 10 carbons in length may be bonded to a silicone atom although 2 to 5 carbon alkyls are preferable.

The inventive flouroalkylpolysiloxanes have beneficial effects as a cosmetic particulate coating when as little as 0.01 weight percent of the coating, with respect to the coated particulate, is used. In excess of 30.0 weight percent of the coating may be used although such great amounts are not necessary.

Flouroalkylpolysiloxanes and products incorporating the inventive coating have a high degree of solvent resistance and retain their excellent stability even when aged at temperatures as high as 45° C.

Surface treatment, in accordance with the invention of pigments, pigment extenders and particulate matter used for decorative and non-decorative cosmetics using substituted fluoroalkylpolysiloxanes results in enhanced lubricity and water repellency (hydrophobicity) and greater adhesion to the skin with no tactile negatives. When dispersed with other materials it gives less color change on the skin and with emulsion systems these surface treated materials are suspended easily and are completely stable even under alkaline conditions.

Treatment of pigments, pigment extenders and other particulate matter may be achieved by the following method in accordance with the invention.

This method of treatment comprises the addition of 0.01 to 30 weight percent (typically found to work well in the range of about two percent) of the fluoroalkylpolysiloxane to the solid material (pigment, pigment extender or other particulate matter) by spraying into a fluidized, agitated filler bed or prilling tower containing the cosmetic raw material. The sprayed powder is then transferred to a mixer such as a PK twin shell blender (with intensifier bar). One may also use a Littleford-Lodige mixer granulator, a ribbon blender, pan mixer, paddle mixer, a vertical screw mixer, turbine mixer, twin rotator mixer or Muller mixer. The mixing is continued in the PK blender mix until adequate treatment is achieved. This may be determined by the degree to which the solid particulates, with their various porosities have absorbed the fluoroalkylpolysiloxanes.

The treated material is then pulverized by using a suitable micropulverizer. One may also employ a hammer mill, cage mill, tumbling ball mill, roller mill, disc mill, fluid energy mill or any suitable micronizer. The milling or pulverizing process is repeated usually 2 to 3 times to obtain uniform and desired particle size. Desired particle size is selected in accordance with the size typically and conventionally required for the particular end product being manufactured.

The treated powders/particulate matter may be composed of any of the following powdered materials as single ingredients or combinations thereof:

Pigments

Organic Colors
Titanium Dioxide
Zinc Oxide
Iron Oxides (Red, Black & Yellow)
Zirconium Oxide
Ultramarine (Blue, Violet & Pink)
Prussian Blue
Chromium Oxides
Chromium Hydroxides
Manganese Violet
Carmine
Ferric Ferrocyanides
Ferric Ammonium Ferrocyanides
Iron Hydroxides Pigment Extenders Talc
Kaolin
Magnesium Carbonate
Calcium Carbonate
Boron Nitride
Sericites
Mica
Aluminium Hydroxide
Bismuth Oxychloride
Magnesium Aluminum Silicate
Silica Beads
Aluminum Silicate Other Particulate Matter Nylons (Polyamides)
Sunscreens
Cellulose
Ceramic Beads
Polymethacrylate polymers and copolymers Ethylene/Acrylates polymers and copolymers
Styrene/Divinylbenzene polymer and copolymers.

The treated powders are then utilized to prepare various cosmetic formulas for such products as eye Shadows, blushers, face powders, lipsticks, mascara, liquid eyelines, cream make-up, liquid make-up, liquid eye shadow, nail polish, treatment skin lotions and creams, multiphase emulsions, lip gloss, eye pencils, lip pencils and rouge.

Four typical make-up formulations using materials coated with the flourinated polysiloxane ar given below. It is noted that some ingredients may be totally dispensed with, additional ingredients may be used and most if not all ingredients may be substituted for.

EXAMPLE 1—1

A typical eye shadow makeup products were prepared using the indicated weight percent of various ingredients. Flouroalkylpolysiloxane treated materials are noted as "treated" in the table below.

| Material | Weight Percent Range | Preferred Composition |
| --- | --- | --- |
| Talc | 70 to 80 | 74.7 |
| Zinc Stearate | 3 to 9 | 6.0 |
| Magnesium Carbonate | 0 to 5 | 2.0 |
| Treated Titanium Dixoide | 1 to 5 | 2.0 |
| Treated Iron Oxides | 0 to 3 | 1.0 |
| Treated Ultramarine Blue | 1 to 15 | 8.0 |
| Squalane | 0 to 10 | 4.0 |
| Mineral Oil | 0 to 5 | 1.0 |
| Lanolin Alcohol | 0 to 3 | 0.5 |
| Preservatives | 0 to 3 | 0.8 |

The manufacturing process comprises mixing the powder ingredients, followed by addition of the liquid-/oil phase and mixing well. The resultant mixture was then pressed into a mold. Suitable results may be achieved by varying ingredients within the ranges indicated above.

EXAMPLE 2—1

A typical blusher makeup product is prepared using the weight percent of the various ingredients indicated below, including flouroalkylpolysiloxane treated materials.

| Material | Weight Percent Range | Preferred Composition |
| --- | --- | --- |
| Treated Talc | 40 to 60 | 47.7 |
| Bismuth Oxychloride | 3 to 15 | 10.0 |
| Mica | 5 to 20 | 18.0 |
| Zinc Stearate | 0 to 10 | 4.0 |
| Treated Titanium Dioxide | 3 to 15 | 10.0 |
| Treated Iron Oxides | 1 to 5 | 2.0 |
| Treated D&C Red 30 Al Lake | 0 to 3 | 0.5 |
| Treated Ultramarine Blue | 0 to 3 | 0.5 |
| Squalane | 0 to 10 | 4.0 |
| Mineral Oil | 0 to 5 | 1.0 |
| Isopropyl Palmitate | 0 to 5 | 1.5 |
| Preservatives | 0 to 3 | 0.8 |

The manufacturing process comprises mixing the powder ingredients, following by addition of the liquid-/oil phase and mixing well. The resultant mixture was then pressed into a mold. Suitable results may be achieved by varying ingredients within the ranges indicated above.

EXAMPLE 3—1

The lipstick formula prepared using treated cosmetic materials is shown in example 3—1 using the weight percent of various ingredients, including fluoroalkylpolysiloxane treated materials.

| Material | Weight Percent Range | Preferred Composition |
| --- | --- | --- |
| Triisocetyl Citrate | 40 to 60 | 51.8 |
| Ozokerite | 0 to 10 | 6.0 |
| Beeswax | 0 to 10 | 6.0 |
| Carnauba Wax | 0 to 5 | 2.2 |
| Candelilla Wax | 0 to 5 | 1.0 |
| Paraffin | 0 to 5 | 1.5 |
| Lanolin Alcohol | 0 to 5 | 2.0 |
| Castor Oil | 5 to 15 | 11.9 |
| Treated Nylon-12 | 0 to 5 | 2.0 |
| Treated D&C Red 6 Ba Lake | 1 to 3 | 1.6 |
| Treated D&C Red 7 Ca Lake | 1 to 3 | 1.7 |
| Treated Iron Oxides | 0 to 3 | 0.6 |
| Treated Bismuth Oxychloride | 0 to 2 | 0.4 |
| BHT | 0 to 2 | 0.5 |
| Preservatives | 0 to 2 | 0.3 |
| Perfume | 0 to 2 | 0.5 |

The waxes and oils are heated to 85° C. The colors, which have been roller milled previously in castor oil blends, are added slowly and the mix is blended all together at 85° C. until uniform then cooled to 70° C. and molded.

EXAMPLE 4—1

A waterproof mascara product was prepared using the weight percent of various ingredients.

| Material | Weight Percent Range | Preferred Composition |
| --- | --- | --- |
| Petroleum Distillate | 35 to 55 | 45.5 |
| Polyethylene | 3 to 10 | 8.0 |
| Treated Nylon | 0 to 5 | 2.5 |
| Candelilla Wax | 2 to 7 | 4.0 |
| Beeswax | 2 to 7 | 4.0 |
| Lanolin | 0 to 5 | 2.0 |
| Genex 216 | 0 to 5 | 2.5 |
| Floral 83 | 0 to 5 | 2.5 |
| Bentone Gel SS71 | 10 to 20 | 16.5 |
| Treated Iron Oxide Black | 5 to 15 | 10.0 |
| Treated Ultramarine Blue | 0 to 5 | 2.0 |
| Preservatives | 0 to 2 | 0.5 |

In a closed mixing vessel, the liquid phase is headed to 75° to 80° C. The waxes are added and the mix is blended until uniform. The pigments are then added and mixture is blended until uniform. The product is cooled to 30° C. then filled into a container.

In summary, the invention provides a cosmetic powder or microparticulate material coated with from 0.1 to 30.0 weight percent of a trifluoroalkylpolysiloxane compound of the general formula:

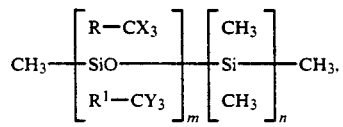

wherein
m is an integer averaging from 1 to 1000;
n is 0 or 1;

R and $R^1$ are alkyl groups of from 1 to 10 carbons;

X is hydrogen or fluorine;

Y is hydrogen of fluorine where at least one of X and Y is fluorine; and the trifluoro groups may be randomly or uniformly disposed over the polysiloxane structure.

While an illustrative embodiment of the invention has been described above, it is, of course, understood that various modifications will be apparent to those of ordinary skill in the art. Such modifications are within the spirit and scope of the invention, which is limited and defined only by the appended claims.

I claim:

1. A cosmetic powder or microparticulate material coated with from 0.01 to 30.0 weight percent of a trifluoralkylpolysiloxane compound of the general formula:

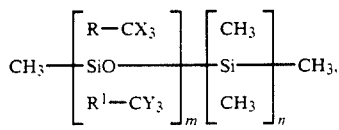

wherein m is an integer averaging from 1 to 1000 n is 0 or 1;

R and $R^1$ are alkyl groups of 1 to 10 carbons;

X is hydrogen or fluorine;

Y is hydrogen or fluorine where at least one of X and Y is fluorine; and the trifluoro groups may be randomly or uniformly disposed over the polysiloxane structure.

2. A cosmetic powder or microparticulate material coated with a triflouropolysiloxane compound as claimed in claim 1, wherein X is hydrogen only.

3. A cosmetic powder or microparticulate material coated with a triflouropolysiloxane compound as claimed in claim 1, wherein m is an integer averaging from 50 to 1000.

4. A cosmetic powder or microparticulate material coated with a triflouropolysiloxane compound as claimed in claim 3, wherein m is an integer averaging from 100 to 500.

5. A cosmetic powder or microparticulate material coated with a triflouropolysiloxane compound as claimed in claim 5, wherein R is an alkyl group comprising 2 to 5 carbons.

6. A cosmetic powder or microparticulate material coated with a triflouropolysiloxane compound as claimed in claim 1, wherein said triflouropolysiloxane compound coating comprises 0.01 to 30.0 weight percent of the coated material.

7. A cosmetic powder or microparticulate material coated with a triflouropolysiloxane compound as claimed in claim 1, wherein m is an integer averaging from 1 to 100.

8. A cosmetic powder or microparticulate material coated with a flouroalkylpolysiloxane compound of the general formula:

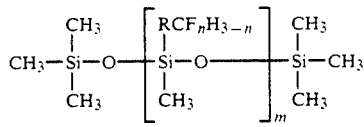

m is an integer averaging from 1 to 500;

n is 0, 1, 2 or 3;

R is an alkyl group of 0 to 10 carbons; and the flouro groups may be randomly or uniformly disposed over the polysiloxene structure.

9. A cosmetic composition comprising a modified powder or microparticulate material as claimed in claim 1.

* * * * *